United States Patent
Matalon

[19]

[11] Patent Number: 5,954,701
[45] Date of Patent: Sep. 21, 1999

[54] BLOOD VESSEL ENTRY INDICATOR

[75] Inventor: Eli Matalon, Ness-Ziona, Israel

[73] Assignee: Vascular Technologies Ltd., Ness Ziona, Israel

[21] Appl. No.: 08/913,791

[22] PCT Filed: Nov. 24, 1996

[86] PCT No.: PCT/IL96/00160

§ 371 Date: Sep. 5, 1997

§ 102(e) Date: Sep. 5, 1997

[87] PCT Pub. No.: WO97/25081

PCT Pub. Date: Jul. 17, 1997

[30] Foreign Application Priority Data

Jan. 5, 1996 [IL] Israel ......................................... 116685

[51] Int. Cl.[6] ................................................ A61M 5/32
[52] U.S. Cl. ............................................................. 604/272
[58] Field of Search ................................ 604/272, 264, 604/280; 73/85, 839

[56] References Cited

U.S. PATENT DOCUMENTS

| | | | |
|---|---|---|---|
| 2,535,998 | 11/1950 | Bierman | 73/389 |
| 2,648,328 | 8/1953 | Hathaway et al. | 128/2.05 |
| 3,473,386 | 10/1969 | Nielsen, Jr. et al. | 73/398 |
| 3,490,441 | 1/1970 | Curtis | 128/2.05 |
| 3,550,583 | 12/1970 | Chiku | 128/2.05 |
| 3,565,056 | 2/1971 | Statham | 128/2 |
| 3,710,781 | 1/1973 | Huthcins, IV et al. | 128/2.05 D |
| 4,036,216 | 7/1977 | Ramsey, III | 128/2.05 D |
| 4,356,826 | 11/1982 | Kubota | 128/630 |
| 4,431,009 | 2/1984 | Marino, Jr. et al. | 128/673 |
| 4,535,773 | 8/1985 | Yoon | 604/51 |
| 4,581,019 | 4/1986 | Curelaru et al. | 604/164 |
| 4,809,704 | 3/1989 | Sogawa et al. | 128/675 |
| 4,952,207 | 8/1990 | Lemieux | 604/164 |
| 5,050,297 | 9/1991 | Metzger | 29/855 |
| 5,098,410 | 3/1992 | Kerby et al. | 604/256 |
| 5,133,358 | 7/1992 | Gustafson et al. | 128/675 |
| 5,290,244 | 3/1994 | Moonka | 604/164 |
| 5,454,374 | 10/1995 | Omachi | 128/673 |
| 5,599,347 | 2/1997 | Hart et al. | 606/42 |

*Primary Examiner*—Manuel Mendez
*Attorney, Agent, or Firm*—Abelman, Frayne & Schwab

[57] ABSTRACT

This invention is a device for detecting and indicating a situation where an intravascular needle (1) has entered a blood conducting vein or artery. The device is to be connected to the distal end of the conduit which includes a female luer connector (2) while the device has a male connector (3). The device includes a sensitive pressure sensor (6) which responds to changes of pressure from the moment of entry of blood into the needle and activates a signal (8).

6 Claims, 2 Drawing Sheets

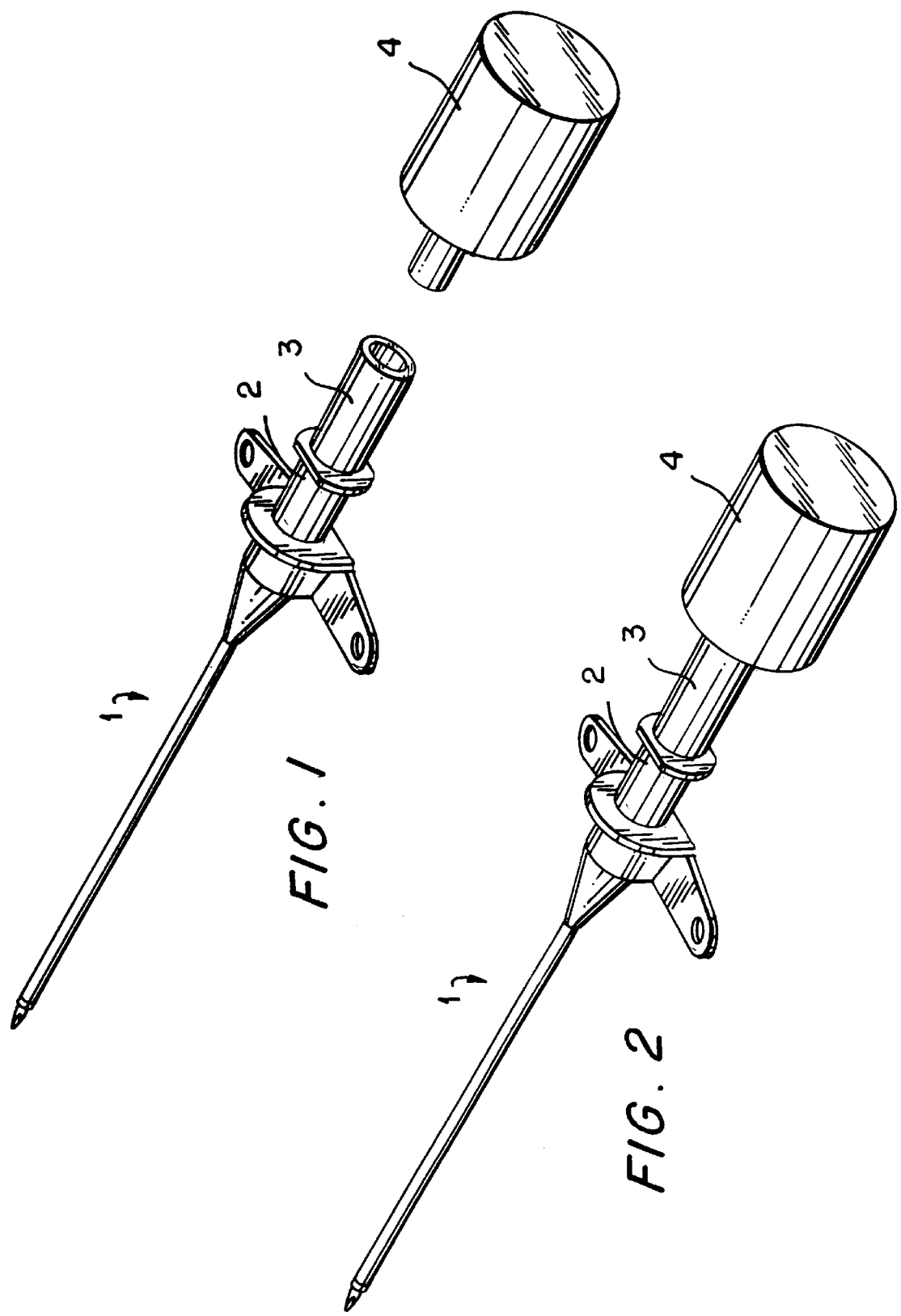

BLOOD VESSEL ENTRY INDICATOR

FIELD OF INVENTION:

The present invention relates to a device for detecting and indicating a situation where an intravascular needle has entered a blood conducting vein or artery, and more particularly to a sound or LED signal that indicates when the needle comes into contact with the pressure of blood within a vein or artery, or any other liquid containing cavity.

The invention is based on a very sensitive sensor which makes it possible to obtain the signal immediately after penetration into the vein or the artery The device according to the invention makes possible of taking visual attention on the puncture spot and not to observe the flashback chamber of the cannula while performing the entry into the patient vessel.

BACKGROUND OF THE INVENTION

Intravenous and arterial cannulas presently in use depend upon a visual observance of blood itself in the hub of the cannula (flashback chamber); After the needle has entered the vein or artery blood does flow through the length of the cannula and fills the flashback chamber in order to indicate that the cannula needle has entered the vessel. The blood according to this method is visible in the chamber after a period of time so the needle may puncture the second wall of the vessel before any sign appears. This may result in improper administration of medication, hemorrhaging, collapse of the vein or artery, or other similar complications.

One method of addressing this situation is disclosed in U.S. Pat. No. 5,030,207. According to that patent a device is provided for indicating when an intravenous needle has entered the vein through the use of a solid fiber optic mounted in the needle for showing visual instantaneous vein entry. The distal end of the fiber optic reflects color, such as red blood to the magnifying system at the rear or proximal end of the fiber optic. The user observes immediate vein entry without any blood flow or exposure to blood. That invention is complicated to manufacture, requires a certain amount of light to work properly, and also forces the user to look and focus at the proximal end of the cannula instead of the puncture point.

Another method of addressing the problem is U.S. Pat. No. 5,314,410 includes a colored flexible membrane disposed within the transparent body of a hypodermic needle that is stretched over the proximal end of the needle cannula. As the needle reaches the inside of the blood vessel, pressure within the vessel is transferred through the cannula to the membrane which moves or inflates indicating entry has been achieve. This device also forces the user to look and focus at the proximal end of the cannula instead of the puncture point.

Both above methods are widely used, however these are somewhat inconvenient to use as the person using the device must look at the device rather than the patient.

In all the above methods the device is part of the cannula in contrary to the present which can be connected to any commercial cannula.

It is thus the main object of the present invention to provide a device which is more reliable because it gives sound signal even at a very low pressure, so that the indication of vessel penetration is prompt. Moreover, with the use of this device the chance of double puncture of the blood vessel decreases.

BRIEF SUMMARY OF THE INVENTION

The device is to be connect to the distal end of the conduit which includes a female luer connection while the device has a male exterior luer connection. It is also possible to connect the device permanently to the needle. When the leading end of the needle enters a blood vessel, blood enters the needle. A sensitive pressure sensor responds to change of pressure from the moment of entry of blood into the needle and activates the signal. The signal may be of a buzzer or whatever similar known device which does emit tones, or a LED or similar visible signal, or an audio visual combination. The signal indication is received quicker than appearance of blood in the transparent chamber.

The present invention enables the recognition of a penetration by a needle of both walls of a blood vessel by means of identification of the decrease of pressure by the sensor.

The exclusion of a need to inspect the chamber allows the user to hold the cannula in a way which amounts to a full covering of the chamber, there being no need to look at it.

The proposed device can be connected to every cannula which has a standard luer connection and does not require whatever constructive change or alteration.

Moreover, the device need not be disposable as there is no contact between the device and blood.

The pressure sensor could be such as an IC semiconductor piezoresistor transducer, or any similar or different sensor.

SHORT DESCRIPTION OF APPENDED DRAWINGS

The invention will now be described with reference to the drawings in which:

FIG. 1 shows in perspective the exterior of the device placed beside a medical cannula of well known type and construction, separate of one another.

FIG. 2 depicts the same parts fully connected with each other.

Figure 3:
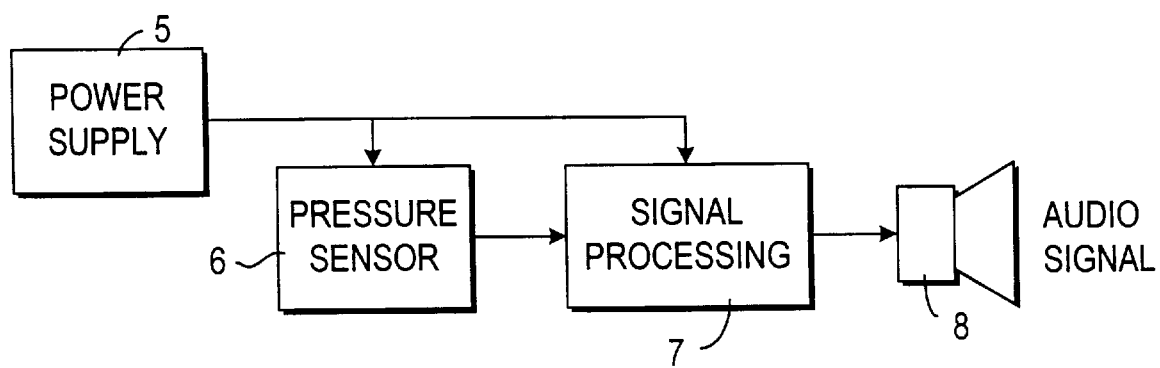

FIG. 3 finally shows by way of a block diagram the active elements of which are enclosed in the casing the exterior of which is depicted in FIGS. 1–2.

The invention will now be described in detail having reference to the drawings.

DETAILED DESCRIPTION OF INVENTION

Turning first to FIGS. 1 and 2, there is provided at the end of the needle part of a medical cannula a female coupling part 2 adapted to receive a male coupling part 3 which in turn extends from a casing 4 in which are located the elements which form the active constituents of the attachment to a medical cannula.

These constituents are depicted in the block diagram of FIG. 3. A source of electric power 5, in practice a minuscule dry battery of the type used in hearing aids or pocket or wrist watches, and a highly sensitive sensor 6 adapted to respond to pressure of a blood stream which enters the needle 1 is connected to said power source 5. Said sensor is connected with a signal processing device 7 which activates a small sound emitter 8 and/or a LED or the like which emits a signal, indicating that the needle 1 has been properly located in the respective vein or artery. In case this should not be so and the needle would have punctured the wall of the blood conduit, its point would obviously emerge into the open and contact with blood pressure would cease, the result being cessation of emittance of warning sound.

The above description relates to a device adapted to be used with a medical needle. It is within the scope of the invention to attach the device permanently to the needle.

Further more the cannula described could also be used to introduce a catheter, and be used for any other liquid containing vessel in the human body.

I claim:

1. A device indicator for a medical cannula or needle for penetration of a living body which indicates by a signal the location of the distal end of a needle which is connected to said device at the time of actual use of the respective cannula when the needle thereof has entered a blood or liquid conducting or containing vessel, said device comprising a housing adapted to be connected to a cannula or needle, within said device there is provided a pressure sensor which is connected to a signal processing element which in turn is connected to a signal emitting means, all components being connected to an electric power source.

2. A device as claimed in claim 1 whereby said device is connected to said cannula or needle by means of a luer connection.

3. A device as claimed in claim 1 whereby said device is integral with said needle.

4. A device according to claim 1 whereof the signal is an audible signal.

5. The device according to claim 1 whereof the signal is a LED.

6. A device as claimed in claim 1 wherein said cannula is used as an introducer for a catheter.

* * * * *